United States Patent [19]

Aberg et al.

[11] Patent Number: 6,110,974

[45] Date of Patent: Aug. 29, 2000

[54] METHODS OF ACCELERATING MUSCLE GROWTH AND IMPROVING FEED EFFICIENCY IN ANIMALS BY USING OPTICALLY PURE EUTOMERS OF ADRENERGIC BETA-2 RECEPTOR AGONISTS, AND FOOD SUPPLEMENTS CONTAINING THE SAME

[75] Inventors: A. K. Gunnar Aberg, Sarasota, Fla.; Paul J. Fawcett, Dunedin, New Zealand

[73] Assignee: Bridge Pharma, Inc., Sarasota, Fla.

[21] Appl. No.: 09/069,512

[22] Filed: Apr. 29, 1998

Related U.S. Application Data

[60] Provisional application No. 60/045,120, Apr. 30, 1997.

[51] Int. Cl.[7] .................................................. A61K 31/135

[52] U.S. Cl. ............................................................. 514/653

[58] Field of Search ............................................... 514/653

[56] References Cited

U.S. PATENT DOCUMENTS

| 5,552,442 | 9/1996 | Maltin | 514/620 |
|---|---|---|---|
| 5,708,036 | 1/1998 | Pesterfield | 514/653 |

*Primary Examiner*—Kimberly Jordan
*Attorney, Agent, or Firm*—Nields, Lemack & Dingman

[57] ABSTRACT

Method for improving health, survival and muscle growth rate of animals, while reducing carcass fat and improving feed efficiency by administering an optically pure eutomer of an adrenergic beta-2 agonist. The invention is also directed to food compositions comprising the adrenergic beta-2 agonists.

6 Claims, No Drawings

METHODS OF ACCELERATING MUSCLE GROWTH AND IMPROVING FEED EFFICIENCY IN ANIMALS BY USING OPTICALLY PURE EUTOMERS OF ADRENERGIC BETA-2 RECEPTOR AGONISTS, AND FOOD SUPPLEMENTS CONTAINING THE SAME

This application claims the benefit of U.S. Provisional Application No. 60/045,120, filed Apr. 30, 1997.

BACKGROUND OF THE INVENTION

Many biologically active molecules exist as enantiomers. Although structurally identical, enantiomers can have different effects in biological systems: one isomer may have specific therapeutic activity while the other isomer may have no therapeutic activity or may have entirely different forms of biological activity.

The form in which adrenergic beta-2 agonist drugs presently are used therapeutically in mammals are as racemic mixtures of two isomers (e.g., R- and S-albuterol; R- and S-salmeterol; R- and S-terbutaline). An R-isomer of a racemic compound is structurally identical to the S-isomer and the isomers differ only in that one isomer is a mirror image of the other. Molecules with two chiral centers have four isomers, e.g., RR-formoterol, SS-formoterol, RS-formoterol and SR-formoterol. The therapeutically active isomers (the eutomers) of beta-2 agonists are the R- or RR-isomers, while the S-or SS-isomers usually do not carry therapeutic activity (distomers). An exception is salmeterol, where both isomers carry adrenergic beta-2 agonistic activity and thus either of the isomers of salmeterol can be regarded as a eutomer.

A therapeutic action of beta-2 agonist drugs is to active adrenergic beta-2 receptors and thereby initiate cellular responses, the most well-known in the relaxation of bronchial smooth muscles. Adrenergic beta agonist drugs also have metabolic effects and increase growth, and such effects may reside in either of the isomers. It has now been shown that the beta-agonist eutomer causes improved muscle growth, while a decrease in carcass fat has been established.

The pharmacological effects and the toxicity of adrenergic beta-agonists varies, depending on the animal species and which drug is studied. The therapeutically inactive S-isomer of albuterol has now been found to be approximately equitoxic to the R-isomer. The S-isomers of albuterol and salmeterol have now been found to be metabolized significantly slower than the R-isomers, causing a prolonged presence of residual S-albuterol and S-salmeterol, respectively, to exist in the body.

The most commonly used therapeutic indication for beta-agonists in man is to treat bronchial spasms in asthmatic individuals. Adrenergic beta-agonist drugs also have been shown to inhibit premature contractions (tocolysis) of the pregnant uterus in humans. The potentially hazardous side effects of albuterol in humans include but are not limited to bronchial hyperreactivity, increased intraocular pressure, uterine hyperreactivity (stimulation of uterine contractions) and teratogenic effects of the drug to the fetus.

SUMMARY OF THE INVENTION

The present invention relates to a method of improving health and muscle growth in animals, especially domestic animals, including fish, by administering the optically pure eutomer of albuterol, terbutaline, clenbuterol, salmeterol, fenoterol and/or formoterol or other beta-2 agonist drugs, while eliminating the side effects caused by the distomer of the drugs and decreasing total drug residues in the body of the animal. The method has proved particularly useful in animals that have demonstrated a propensity for health disorders, in which the health status and the survival rate is improved by eutomers of beta-2 agonists, and in animals that have a muscular growth rate that needs to be improved and in cases where improved feed efficiency is sought. In cases of chicken, pigs, sheep, cows and fish and all other animals that enter the food chain, there is a risk of side effects induced by the drugs in other, usually higher order animals eating the meat of those animals that have been slaughtered. Very long biological half-lives of the distomers of albuterol and salmeterol may be found in domestic animals, including farmed fish, and consequently, the carcass of such animals to which these drugs have been administered contain significant tissue concentrations of S-albuterol and S-salmeterol, for example, after slaughter. R-albuterol and R-salmeterol, on the other hand, were found to have shorter biological half-lives, and consequently less drug residue is found in the bodies of slaughtered animals that have been administered the pure R-isomer of those compounds. Since the R-isomers of beta-agonists such as albuterol, clenbuterol and terbutaline have not been shown to carry such side effects as bronchial hyperreactivity, increased intraocular pressure, increased uterine contractility or teratogenic activity, the R-isomer is significantly less toxic than the racemate of the compound. Thus, administering to the animals appropriate doses of the optically pure eutomers will not cause harm to the animal, will not leave drug residues of distomers in the carcass and will not cause harm, induced by the distomer, in other, usually higher order animals such as humans eating the slaughtered animals. The present method provides a safe, effective method for treating animals, such as birds, including chicken and turkeys, mammals, including horses, cows, pigs and sheep and farmed fish, without causing side effects in the animal or in the mammal eating the animal or in the unborn offspring of the mammal eating the animal, the purpose of such treatment being improved health, survival rate and/or growth rate.

The present invention also relates to animal feed or nutritive supplements for animals, such as warm-blooded animals, containing one or more of the optically pure eutomers discussed above. In one embodiment, the nutritive supplement is a protein-containing food fortified with one or more optically pure eutomer of an adrenergic beta agonist.

DETAILED DESCRIPTION OF THE INVENTION

The R-isomers of albuterol and other adrenergic beta-agonists have now been found to improve survival and muscle growth in animals, including farmed fish. The S-isomers of albuterol and other adrenergic beta-agonists have been found to cause serious side effects and the distomers have now been found to occur in the carcass of slaughtered animals, including farmed fish, after administration of the racemates to the animals.

The present invention relies on the activity of the eutomers of albuterol, terbutaline, clenbuterol, salmeterol, fenoterol and formoterol to provide improved health and increased body weight in domestic animals, including farmed fish, while simultaneously minimizing or eliminating side effects that are caused by the distomer of the beta-agonists in said animal, in mammals such as people eating the slaughtered animal and in the unborn of spring of a pregnant mammal eating the slaughtered animal. The risk for side effects that reside in the distomer—e.g., bronchial and uterine hyperreactivity induced by the distomer of said beta-agonist—are minimized or eliminated by using the optically pure eutomer instead of the racemic mixture. As an example, bronchial hyperreactivity and cough induced by S-albuterol in horses is avoided by using the optically pure eutomer. In the present method, an optically pure eutomer of albuterol, terbutaline, clenbuterol, salmeterol, fenoterol or formoterol, substantially free of their corresponding distomers, can be administered alone, or in combination with at least one other drug in adjunctive treatment, to animals in whom relief from health disorders or increased body weight development is desired. As examples the R-isomer of albuterol as used herein refers to the optically pure R(+)-isomer of α'[tert]butylamino}methyl]-4-hydroxy-m-xylene-α,α'-diol, and to any biologically acceptable salt or rester thereof, the R-isomer of clenbuterol refers to the optically pure R(+)-isomer of 4-amino-α-[(tert-butylamino) methyl]-3,5-dichlorobenzyl alcohol, and to any biologically acceptable salt or ester thereof, the R-isomer of salmeterol refers to the optically pure R(+)-isomer of 4-hydroxy-α-[[[6-(4-phenylbutoxy)-hexylo]amino]methyl]-m-xylene-α, α'-diol and to any biologically acceptable salt or ester thereof, and the R-isomer of terbutaline refers to the optically pure R(+)-isomer of 1-(3,5-dihydroxyphenyl)-2-(tert-butylamino)ethanol, and to any biologically acceptable salt or ester thereof. The terms "optically pure" or "substantially free of the S-enantiomer" as used herein means that the composition contains at least 85% by weight of the R-isomer of a beta-agonist and 15% by weight or less of the S-isomer; preferably the "optically pure" drug consists of at least 99% of the eutomer.

Optically pure adrenergic beta-agonists are readily obtainable by methods known to those skilled in the art, e.g., by synthesis from an optically pure intermediate or resolution of the racemic compound into its isomers.

In the present method, the optically pure eutomer of albuterol, clenbuterol, salmeterol or terbutaline is administered to an animal, in which improved health, improved survival, improved muscular growth rate and/or improved feed efficiency is sought. For example, R-albuterol is administered to an animal to correct or improve a health disorder, such as for example metabolic disorders or to accelerate the muscle growth rate or prophylactically to improve the health status or the animal's muscle growth rate.

In the present method, the optically active R-isomer of albuterol, terbutaline, clenbuterol, salmeterol, fenoterol or formoterol can be administered by inhalation, parenterally, subcutaneously, intravenously, intramuscularly orother injection or infusion, orally, topically, rectally or via an implanted reservoir containing the drug. The form in which the drug will be administered (e.g., inhalant, powder, granulate, tablet, capsule, solution, emulsion, etc.) will depend on the route by which it is administered. The preferred route of administration is the oral route, with the eutomer of a beta-2 agonist mixed into the feed of the animals. The quantity of the drug to be administered will be determined on an individual basis, and will be based on the pharmacological potency of the drug, the route of administration, and at least in part in consideration of the animal's size, the severity of the symptoms to be treated and the results sought. In general, quantities of the optically pure eutomer sufficient to improve health, survival, muscle growth and/or feed efficiency will be administered. The actual dosage (quantity administered at a time) and the number of administrations per day will depend on the pharmacokinetic property of the drug and the metabolism of the drug in the body of the specific animal species. For example, about 10 to 3000 micrograms of the optically pure R(-)-isomer of albuterol or terbutaline may be given by various forms of inhalation devices, 0.01 to 200 milligrams may be given by the oral route (e.g., as powders, granulates or liquids) one to four times per day and may be an adequate dose in most animals to produce the desired effect. The doses of R-salmeterol and R-clenbuterol may be lower and the dosing can also be less frequent than is the case with R-albuterol and R-terbutaline. Drug doses may be higher or lower and administration may take place more or less frequently than indicated above, as determined by the caring individual. The drugs may also be mixed into feed that may be made available to the animals ad lib. Animals may also be administered a long-acting drug, that is substituted with a short-acting drug during the time period prior to the slaughter.

In the method of the present invention, the optically pure eutomer of a beta-2 agonist will be prepared as a dry powder or a granulate and added to the animal feed, such as by mixing. The drug can be pre-mixed into the feed according to any of the methods known to those skilled in the art, or may be mixed or blended into the feed at the time of feeding.

In the method of the present invention, the optically pure R-isomer of albuterol, clenbuterol, salmeterol or terbutaline or the RR-isomer of formoterol or fenoterol, can be administered together with one or more other compound(s). For example, various antibacterial agents, growth factors, hormones, etc. can be given with or between the doses of the eutomeric beta agonist. Compounds that improve or prolong the therapeutic effect of R-albuterol, R-salmeterol or R-terbutaline, e.g., compounds that inhibit the metabolic degradation of the compound (such as acetaminophen), may also be co-administered with the eutomeric beta agonist. The two (or more) drugs (the optically pure active isomer of the beta agonist, together with the other drug(s)) can be administered in one composition or as separate entities. For example, they can be administered in a single capsule, tablet, granulate, powder, or liquid, mist, aerosol, injection, etc. or as individual drug formulations. The components included in a particular formulation, in addition to the optically pure R-isomer or isomers and another drug or drugs, are determined primarily by the manner in which the composition is to be administered. For example, a composition to be administered in liquid form can include, in addition to the drug(s), a liquid carrier, an emulsifying agent, a flavoring agent, an antibacterial or a bacteriostatic agent and/or a coloring agent. A formulation to be administered in powder form or as a granulate can include a filler (e.g., lactose), a binder (e.g., carboxymethyl cellulose, gum arabic, gelatin), an adjuvant, a flavoring agent, and/or a coloring agent.

In general, according to the method of the present invention, the optically pure eutomers of albuterol, clenbuterol, salmeterol, formoterol or terbutaline, alone or in combination with each other and/or with other drug(s), is administered to animals, including farmed fish, periodically or continuously as necessary to improve health, survival or muscle growth (weight gain) and to reduce carcass fat or to improve feed efficiency.

The food composition of the present invention is not particularly limited, and will depend upon the identity of the animal consuming the feed. Generally, the food composition is a protein-containing food, having blended therein one or more of the optically pure eutomers of the present invention. The food composition may contain fat, sugars, vitamins or other nutritionally valuable ingredients.

The present composition, feed and method provide effective treatment while eliminating the undesired side effects induced by the distomer in racemic albuterol, clenbuterol, salmeterol, terbutaline, fenoterol or formoterol, in the animal given the drug and in other, usually higher order animals eating the animal after it has been slaughtered. These side effects include bronchial hyperreactivity, increased uterine contractility, increased intraocular pressure, central nervous system effects such as tremor, shakiness, and dizziness, and cardiovascular effects. In addition, teratogenic effects associated with racemic albuterol are considered to reside in the distomer of the drug. Thus, by the administration of the optically pure eutomer of albuterol, clenbuterol, salmeterol, fenoterol, terbutaline or formoterol, the side effects of the corresponding distomer, which can be of prolonged duration, will be avoided.

Those skilled in the art will recognize, or be able to ascertain using no more than routine experimentation, many equivalents to the specific embodiments of the invention described herein. Such equivalents include the active isomers of other drugs with beta-2 adrenergic agonistic properties, such as for example hexoprenaline, isoprenaline, riniterol, isoetharine, metaproterenol, reproterenol, cimaterol, procaterol, carbuterol, tulobuterol, pibuterol, mabuterol, bitolterol and bambuterol. Also included are eutomers of beta-2 agonists under development, such as broxaterol, etanterol, imoxiterol, namiterol, picumeterol, RP 58802, RU 42173 and ZK 90055. Those skilled in the art will realize that there are many pharmaceutically acceptable salt forms of the drugs of the invention, such as for example sulfate, fumarate, hydrobromide, dihydrochloride, methanesulphonate, hydroxynaphthoate, hydrochloride or where appropriate, one or other of the hydrate forms thereof, see Merck Index 11th edition (1989) items 9089, 209, 3927, 4628, 8223, 5053, 5836, 8142, 2347, 7765, 1840, 9720, 7461, 1317, 4159 and 963 and references cited therein, and AM. Rev. Resp. Dis. 1988, 137: (4;2/2) 32, the disclosure of which are herein incorporated by reference.

Those skilled in the art will realize that eutomers of adrenergic beta agonists may improve muscle growth and decrease body fat in humans as in other mammals, and this indication for eutomers of beta agonists in humans is included in the present invention.

What is claimed is:

1. A method of feeding livestock animals, comprising administering thereto an effective amount of the optically pure eutomer of the adrenergic beta-2 agonist albuterol, while minimizing or eliminating the side effects residing in the corresponding distomer.

2. The method of claim 1, wherein said animal is selected from the group consisting of birds, cows, pigs, horses, sheep and farmed fish.

3. A method of improving feed efficiency in livestock animals, comprising administering thereto an effective amount of the optically pure eutomer of the adrenergic beta-2 agonist albuterol, while minimizing or eliminating the side effects residing in the corresponding distomer.

4. The method of claim 3, wherein said animal is selected from the group consisting of birds, cows, pigs, horses, sheep and farmed fish.

5. A method of improving muscle growth and decreasing body fat in livestock animals, comprising administering thereto an effective amount of the optically pure eutomer of the adrenergic beta-2 agonist albuterol, while minimizing or eliminating the side effects residing in the corresponding distomer.

6. A food composition for livestock animals comprising the admixture with protein-containing food materials of the optically pure eutomer of the adrenergic beta-2 agonist albuterol.

* * * * *